United States Patent [19]

Thurtell et al.

[11] Patent Number: 5,331,409
[45] Date of Patent: Jul. 19, 1994

[54] TUNABLE DIODE LASER GAS ANALYZER

[76] Inventors: George Thurtell, 38 University Ave. West, Guelph, Ontario, Canada, N1G 1N4; Gary Kidd, 11 Batterswood Ct., Kitchener, Ontario, Canada, N2A 3S3; Grant Edwards, 378 Willard Ave., Toronto, Ontario, Canada, M6S 3R5

[21] Appl. No.: 897,703

[22] Filed: Jun. 12, 1992

[51] Int. Cl.⁵ .............................................. G01N 21/61
[52] U.S. Cl. ..................................... 356/437; 250/345; 356/440
[58] Field of Search ................ 250/343, 345; 356/435, 356/437, 439, 440

[56] References Cited

U.S. PATENT DOCUMENTS

| | | | |
|---|---|---|---|
| 3,742,382 | 6/1973 | Smith | 331/94.5 |
| 3,995,960 | 12/1976 | Fletcher et al. | 356/204 |
| 4,059,356 | 11/1977 | Kebabian | 356/204 |
| 4,061,918 | 12/1977 | Preir et al. | 250/343 |
| 4,234,258 | 11/1980 | Margolis et al. | 356/437 |
| 4,412,445 | 11/1983 | Spellicy | 73/24 |
| 4,489,239 | 12/1984 | Grant et al. | 250/339 |
| 4,516,857 | 5/1985 | Preston et al. | 356/418 |
| 4,535,241 | 8/1985 | Eberhardt | 250/339 |
| 4,549,080 | 10/1985 | Baskins et al. | 250/343 |
| 4,684,258 | 8/1987 | Webster | 356/409 |
| 4,701,607 | 10/1987 | El-Hanany et al. | 250/205 |
| 4,730,112 | 3/1988 | Wong | 250/343 |
| 4,849,637 | 7/1989 | Cerff et al. | 250/345 |
| 4,934,816 | 6/1990 | Silver et al. | 356/409 |
| 4,990,780 | 2/1991 | Lee et al. | 250/343 |

OTHER PUBLICATIONS

Kemeny et al, "Utilization of Tunable Infrared Diode Lasers For the Determination of Labelled Molecules in Gas Mixtures" 1980 (no month).

Reid et al, "Sensitivity limits of a tunable diode laser spectrometer with application to the detection of $NO_2$ at the 100-ppt level", Applied Optics, Oct. 1980.

Primary Examiner—Richard A. Rosenberger
Attorney, Agent, or Firm—Wells, St. John, Roberts, Gregory & Matkin

[57] ABSTRACT

A tunable laser trace gas analyzer determines the concentration of a target gas in a sample by comparison to a reference gas having a known concentration of the target gas. The trace gas analyzer includes a wavenumber-tunable laser and a gas receiving assembly through which the laser beam is transmitted. The gas receiving assembly comprises a sample gas chamber and a reference gas chamber. Radiation intensity sensors are positioned at remote ends of the sample gas chamber and the reference gas chamber to detect the intensity of the laser transmissions through the sample and reference gases. A beam splitter is positioned within the gas receiving assembly to direct one laser beam portion to one of the radiation intensity sensors and another laser beam portion to the other radiation intensity sensor. The concentration of the target gas in the sample is determined by repetitively modulating the laser drive current to cyclicly vary the laser emission wavenumber about an absorption line of the target gas. The operation of the analyzer is refined by periodically disabling the laser by interruption of the laser drive current before each repetition of the drive current modulation and subsequently overdriving the laser with an increased drive current before the drive current modulating step.

48 Claims, 4 Drawing Sheets

TUNABLE DIODE LASER GAS ANALYZER

TECHNICAL FIELD

This invention relates to measuring trace quantities of a target gas in the presence of other gases using infrared (IR) absorption characteristics unique to the target gas.

BACKGROUND OF THE INVENTION

Gas absorption spectroscopy is performed by measuring the percentage of light which passes through a gas sample at given light wavelengths. Particular gases exhibit characteristic light absorption responses as the wavelength of the light passing through the gas is varied. Gases can be identified by these responses.

Such identification is typically performed by identifying the presence of one or more absorption "lines" in a gas sample. An absorption line is a narrow band of light wavelengths or wavenumbers at which the gas absorbs or attenuates light. A given gas usually has a number of absorption lines at different wavenumbers.

The concentration of a target gas in a gas sample of unknown composition can be determined by the relative light absorption of the sample at wavenumbers corresponding to an absorption line of the target gas. The relationship between molecular concentration and the absorbing effect of a single absorption line is well known.

In general, the molecular concentration N of a target gas in a gas sample can be determined by making two measurements at a wavenumber corresponding to an absorption line: (1) the intensity of light transmitted through the target gas; and (2) the intensity of light transmitted through the same distance in the absence of the target gas. The ratio of these two measurements is defined as transmittance.

The success of these measurements depends on the availability of a stable source of monochromatic or narrow-bandwidth light-light having a very narrow range of wavenumbers. Optical filters or monochromators can be used to supply relatively narrow-bandwidth light. However, light produced in this way typically has a bandwidth larger than an absorption line itself. Accordingly, measurement systems using filters or monochromators typically average measurements over several or many absorption lines. Because of this, these measurement systems are subject to light absorption from interfering gases.

Lasers have been used in recent years as light sources for gas spectroscopy. Lasers produce a light beam having a very narrow frequency bandwidth. Because of this, an instrument using a laser as a light source is able to measure transmittance over a single absorption line. Such transmittance measurements are more accurate than measurements using broadband sources of light. Optical filters or monochromators are not required in order to achieve this accuracy.

However, the accuracy of gas concentration measurements remains limited by other factors. For example, calculating molecular concentration from the two measurements mentioned above requires knowledge of the "ideal" absorption characteristics of the target gas. These characteristics must be measured from a pure gas sample with a very high degree of accuracy. A further complication, however, is that such characteristics are variable with both the temperature and pressure of the gas. This means not only that the absorption response characteristics must be predicted or measured for the pure gas under varying temperature and pressure, but also that the pressure and temperature of the gas sample must be measured to obtain meaningful results. The need for such measurements adds a degree of uncertainty to the calculations, reducing accuracy.

Another limitation relates to the devices and control circuits used for measuring transmitted laser intensities. Typically, some form of radiation intensity sensor is used to measure the intensity of the laser beam after it has been transmitted through the gas sample. An electronic amplification circuit is normally associated with the sensor. In order to make accurate measurements of the transmitted light intensities, background or reference values must first be obtained from the sensor and associated electronics with the laser disabled. Such reference values represent the portion of subsequent readings which is attributable to background sources such as ambient light and amplifier biases. The reference values change with varying ambient light and temperature, as well as with sensor and amplifier drifting.

Because of the variable background values, reference measurements must be made at frequent intervals to ensure accuracy. A convenient way to make such a measurement in a laser system is to disable drive current to the laser, thus eliminating the laser beam. However, this practice causes further complications. When the drive current to the laser is interrupted the laser components immediately begin to cool. Upon resumption of the drive current a finite time is required for the intensity of the laser beam to asymptotically approach its previous operating state. During this finite time the laser frequency changes rapidly. Measurements made during this time are therefore of no value. Rather, measurements must be delayed until the laser has reached its equilibrium state. This can often take as long as or longer than the desired measurements themselves.

The constraints described above severely limit the sensitivity and accuracy of most laser-based gas measurement systems. To increase sensitivity, many such systems use one or more "White cells" to increase the effective path length of the laser beam through the sample gas. A White cell is a sample chamber which reflects the laser beam back and forth a number of times through the sample gas before an intensity measurement is performed. A disadvantage of White cells is that they increase the chances for laser fringing. They are also large and delicate, complicating optical focusing. White cells also add significant cost to a system.

BRIEF DESCRIPTION OF THE DRAWINGS

A preferred embodiment of the invention is described below with reference to the accompanying drawings in which.

DETAILED DESCRIPTION OF THE PREFERRED EMBODIMENT

This disclosure of the invention is submitted in furtherance of the constitutional purposes of the U.S. Patent Laws "to promote the progress of science and useful arts." U.S. Constitution, Article 1, Section 8.

Figure 1:
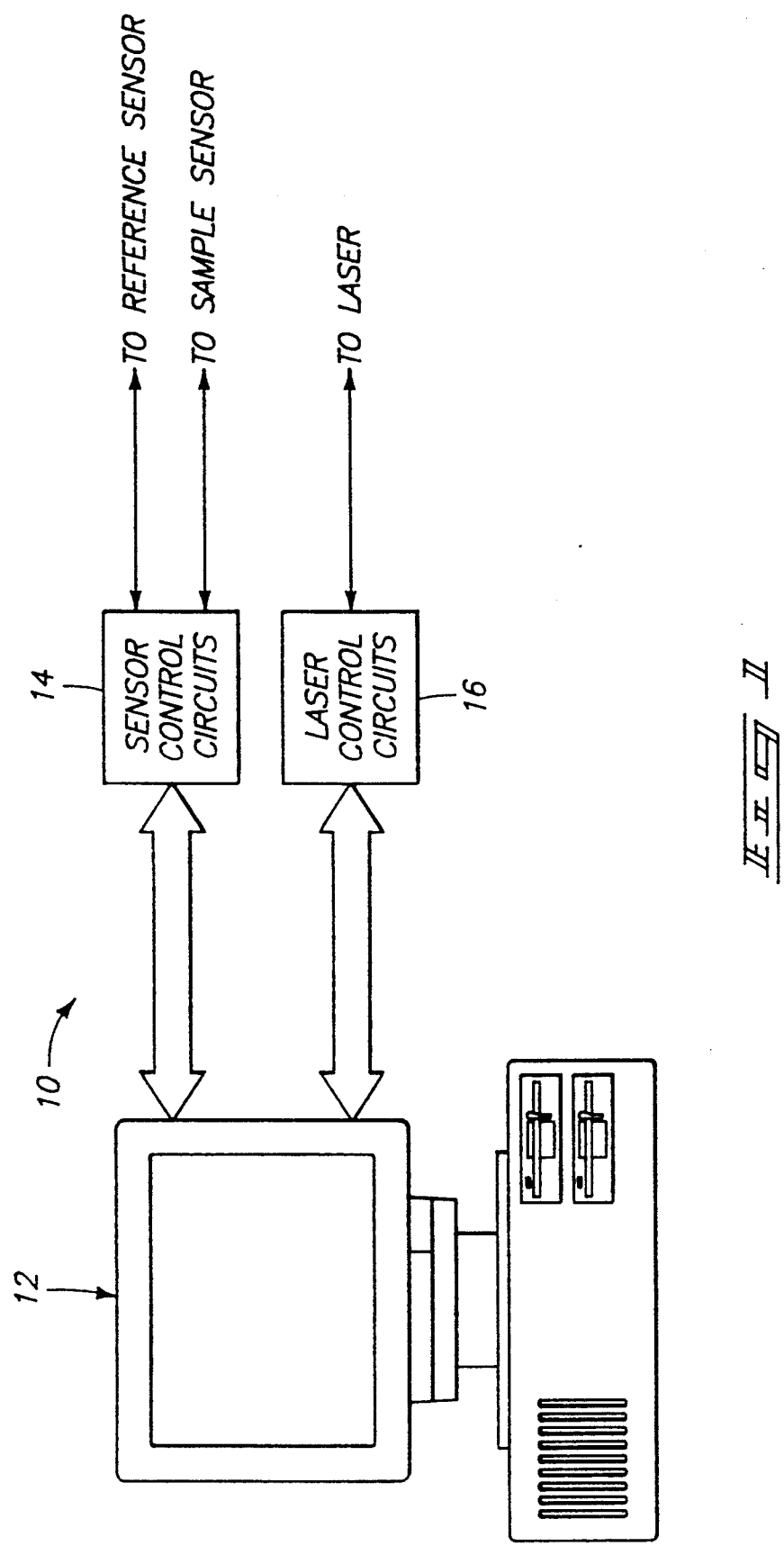
FIG. 1 is a block diagram of trace gas analyzer electronic control system in accordance with a preferred embodiment of this invention.
Figure 2:
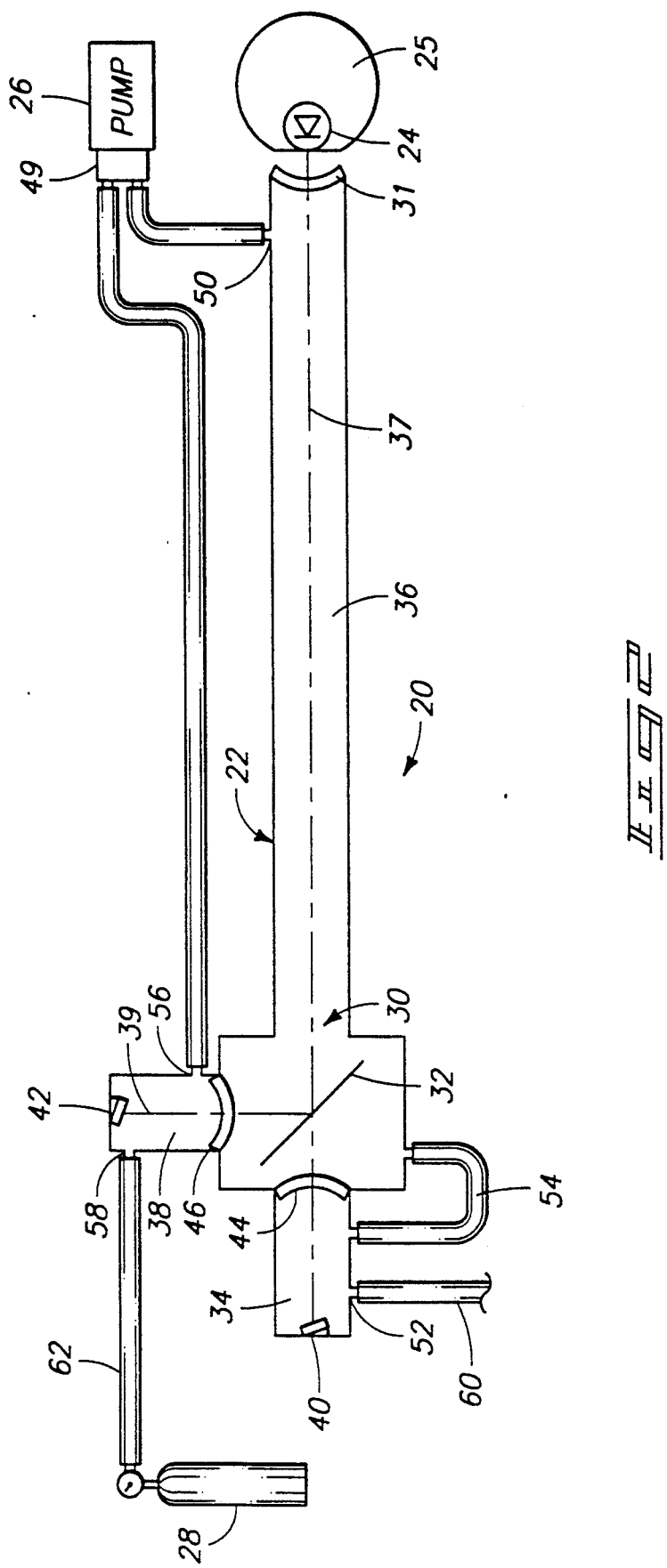
FIG. 2 is a diagram of a trace gas analyzer measurement assembly in accordance with a preferred embodiment of this invention.

FIGS. 1 and 2 show a preferred embodiment of a trace gas analyzer according to this invention for determining the concentration of a target gas in a sample by comparison to a reference gas having a known concentration of the target gas. The trace gas analyzer comprises an electronic control system 10, shown in FIG. 1, and a measurement assembly 20, shown in FIG. 2. Measurement assembly 20 includes a gas receiving assembly 22, a laser 24, a vacuum pump 26, and a reference gas supply or source 28.

Control system 10 includes a general purpose desktop computer 12. Computer 212 communicates with analog interface modules such as sensor control circuits 14 and laser control circuits 16. The analog interface modules allow computer 12 to control various physical parameters of the trace gas analyzer as well as to detect or sense other parameters such as light or radiation intensity.

Laser 24 is a wavenumber-tunable diode laser. One specific example of a suitable laser is lead-salt laser model L5621 manufactured by Laser Photonics of Bedford, Mass. Such a laser emits a laser beam which is typically tunable over a range of about 100 wavenumbers. Different models of tunable diode lasers are available for different wavenumber emission ranges. The particular model chosen is dependent upon the absorption characteristics of the gas being detected.

The wavenumber of the laser beam emitted from laser 24 is dependent on both the temperature of laser 24 and the drive current applied to laser 24. Accordingly, laser beam wavenumber modulation could conceivably be achieved by modulating either the laser temperature or the laser drive current. However, modulating the laser temperature is slow due to the large thermal mass associated with the laser. Therefore, the temperature of laser 24 is kept constant while varying the drive current to modulate wavenumber.

In order to maintain a constant laser temperature, laser 24 is mounted on the end of a cold finger 25 which is in turn cooled by a liquid nitrogen dewar (not shown). This mounting arrangement provides a large thermal mass for the finger and laser, as well as low thermal resistance between the laser and the liquid nitrogen.

An electrical heater (not shown) and two temperature-sensing silicon diodes (not shown) are mounted near the middle of the cold finger 25 for precise control of the laser temperature. A temperature control circuit within laser control circuits 16 can effectively maintain the operating temperature of laser 24 to within one thousandth of a degree Kelvin or less of a chosen constant temperature. The temperature control circuit is implemented primarily with analog circuits for fast response. An analog reference voltage is supplied to the circuit from computer 12 by a digital-to-analog converter included in the laser control circuits 16.

The drive current of laser 24 is controlled by laser control circuits 16 to periodically scan the laser beam across a chosen center wavenumber. Discrete waveform data points are held in a control circuit buffer and supplied sequentially to digital-to-analog converters within laser control circuits 16. The digital-to-analog converters produce a laser control voltage which is translated into a current and supplied to laser 24. The data points correspond to discrete wavenumbers emitted by laser 24 to form a repetitive laser waveform. Varying the laser drive current also affects the intensity of the emitted laser beam. This is a factor which must be considered in subsequent measurement steps.

Gas receiving assembly 22 comprises three distinct sub-chambers or cells through which the laser beam is transmitted. A sample gas chamber 30 for receiving a gas sample being tested extends longitudinally from laser 24. A beam splitter 32 is positioned within sample chamber 30. Sample chamber 30 is divided into a first sample sub-chamber or cell 34, between detector 40 and lens 44, and a second sample sub-chamber or cell 36, between lens 44 and lens 31.

First sample cell 34 forms an optical path through the gas sample along a first longitudinal axis shown as broken line 37. Second sample cell 36 is positioned between beam splitter 32 and laser 24, being aligned along the first longitudinal axis (line 37) to form an optical path also leading through the gas sample along first longitudinal axis 37. Second sample cell 36 is preferably longer than first sample cell 34 by a factor of about thirty. The specific length is chosen to minimize the effects of fringing and to provide sufficient attenuation or absorption through the sample gas for attaining the desired measurement sensitivity.

A reference gas chamber or cell 38, for receiving a reference gas, forms an optical path through the reference gas along a second longitudinal axis shown as broken line 39. Reference cell 38 is positioned relative to first sample cell 34 so that the first and second longitudinal axes intersect each other, preferably at a right angle. Reference cell 38 is therefore preferably at a right angle to sample chamber 30.

A columnating lens 31 is positioned at the near end of sample chamber 30 adjacent to laser 24. Columnating lens 31 directs the laser beam from laser 24 through second sample cell 36.

Beam splitter 32 is positioned at the intersection of the first and second longitudinal axes and in the path of the laser beam. The transmitted beam passes from laser 24 through second sample cell 36 to beam splitter 32. Beam splitter 32 directs a first portion of the laser beam through the sample in first sample cell 34 along the first longitudinal axis. It directs a second portion of the laser beam through the reference gas in reference cell 38 along the second longitudinal axis. Beam splitter 32 is preferably a beam splitting optical flat of barium fluoride or other suitable material with an anti-reflection coating on one surface. Depending on the material used, between 8% to 40% of the laser beam is reflected from beam splitter 32 into reference cell 38. The remaining portion of the laser beam passes through beam splitter 32 into first sample cell 34.

Beam splitter 32 is positioned within sample chamber 30 so that it is surrounded only by the sample gas. Because of this configuration, the laser beam, once past columnating lens 31, passes only through sample gas or reference gas. In addition, gas receiving assembly 22 provides a single, non-reflecting laser beam path through the sample and reference gases. No White cells are required or used, thus reducing the possibilities of laser fringing while also providing enhanced durability in comparison to known prior art systems.

First and second radiation sensors 40 and 42 are positioned at the far or remote ends of sample chamber 30 and reference chamber 38, respectively. They monitor the intensities of the first and second portions of the laser beam after transmission through the sample and reference cells, respectively. Radiation sensors 40 and 42 have active surfaces which are mounted at an acute angle (preferable seventy degrees) to the first and second longitudinal axes 37, 39 to reduce the effect of reflections on fringing.

Focusing lenses 44 and 46 are located adjacent to beam splitter 32. Beam splitter 32 directs the first laser beam portion to first radiation sensor 40 through focusing lens 44 and the second laser beam portion to second radiation sensor 42 through focusing lens 46.

Exemplary radiation sensors 40 and 42 are mercury cadmium teluride detectors which are available from EG&G Judson of Montgomeryville, Pa., although other types of light detectors are also available. The outputs of sensors 40 and 42 are amplified by low-noise voltage amplifiers (not shown) and supplied to computer 12 through sensor control circuits 14. Sensors 40 and 42 are maintained at a constant temperature by conventional Peltier coolers (not shown) to ensure measurement accuracy. Sensor control circuits 14 preferably contain hybrid analog/digital control loops for precisely controlling the temperatures of sensors 40 and 42.

A vacuum pump 26 continuously draws sample gas and reference gas through sample chamber 30 and reference chamber 38, respectively. Vacuum pump 26 has a common vacuum manifold 49 which is connected to both sample chamber 30 and reference chamber 38 to ensure that equal vacuum is supplied to both chambers. Sample chamber 30 has an outlet port 50 at one end which is connected to manifold 49. An inlet port 52 at the other end of sample chamber 30 is connected to a source of sample gas such as ambient air through a sample gas inlet tube 60. A tube 54 forms an open connection between the first and second sample cells 34 and 36.

Reference chamber 38 has an outlet port 56 which is connected to manifold 49 and an inlet port 58 which is connected to a known source of reference gas such as reference gas supply 28 through a reference gas inlet tube 62.

In operation, computer 12 controls the drive current and corresponding transmission wavenumber of laser 24 through laser control circuits 16. A sample gas, such as ambient air, is continuously circulated through sample chamber 30. A reference gas, containing a known concentration of a known target gas, is continuously circulated through reference chamber 38. The two gases are maintained at an equal pressure by their common connection to manifold 49 and at an equal temperature by thermal coupling between sample gas inlet tube 60 and reference gas inlet tube 62.

The more general methodical aspects of this invention include a method of operating a wavenumber-tunable laser, such as diode laser 24, to determine light absorption characteristics of a sample gas. Such a method includes transmitting the laser beam from the tunable laser 24 through the sample gas to first radiation sensor 40. The method further includes repetitively ramping the laser drive current from a beginning ramp current value to an ending ramp current value to cyclicly vary or modulate the laser beam wavenumber over a narrow wavenumber modulation band.

The method of operating a tunable laser also includes periodically disabling laser 24 by interrupting the laser drive current applied through laser control circuits 16 before each repetition of drive current ramping. A subsequent step includes overdriving laser 24 with an increased drive current immediately before each drive current ramping repetition to shorten the time required to restore laser 24 to its equilibrium excitation state. The increased drive current applied to laser 24 during this overdriving step is greater than the beginning ramp current.

Additional steps include directing a portion of the laser beam through a reference gas to a second radiation sensor 42 and monitoring the intensity of the laser beam at the second radiation sensor 42. A further step includes analyzing the measured intensity of the laser beam at the second radiation sensor 42 to identify the target gas absorption line. The results of this analysis are then used in repetitively adjusting the wavenumber modulation band supplied in the laser beam so that the absorption line of the target gas is approximately centered within the modulation band.

More specific operational aspects of this invention include determining laser transmittance through the sample gas at an absorption line of the target gas. The laser operates as described immediately above to provide repetitive current and wavenumber modulation, laser disabling, and laser overdriving.

Laser transmittance is determined by measuring unabsorbed laser transmission intensities during each wavenumber modulation at discrete laser transmission wavenumbers corresponding to target gas absorption line wavenumbers. A preferred method also includes measuring lower and upper unabsorbed laser transmission intensities during the wavenumber modulation at lower and upper wavenumbers which are below and above the target gas absorption line wavenumbers, respectively. Unabsorbed laser transmission intensities at wavenumbers between the lower and upper laser transmission wavenumbers are determined by interpolation from the lower and upper unabsorbed transmission intensities.

A further operational feature of this invention includes determining concentration of the target gas within the sample gas. This determination includes comparing the laser transmittance through the sample gas to the laser transmittance through a reference gas of known target gas concentration.

The preferred method of determining target gas concentration includes splitting the laser beam with beam splitter 32 to direct a sample laser transmission through a gas sample and a reference laser transmission through a reference gas sample. Sample and reference gas absorbances are determined from the intensities of the sample and reference beams at the first and second radiation sensors 40, 42. The absorbances are then compared to determine the molecular concentration of the target gas in the gas sample.

Accurate results be can be obtained by ratioing the measured sample and reference absorbances to determine the molecular concentration of the target gas in the sample without requiring temperature and pressure measurements of the gases.

Figure 3:
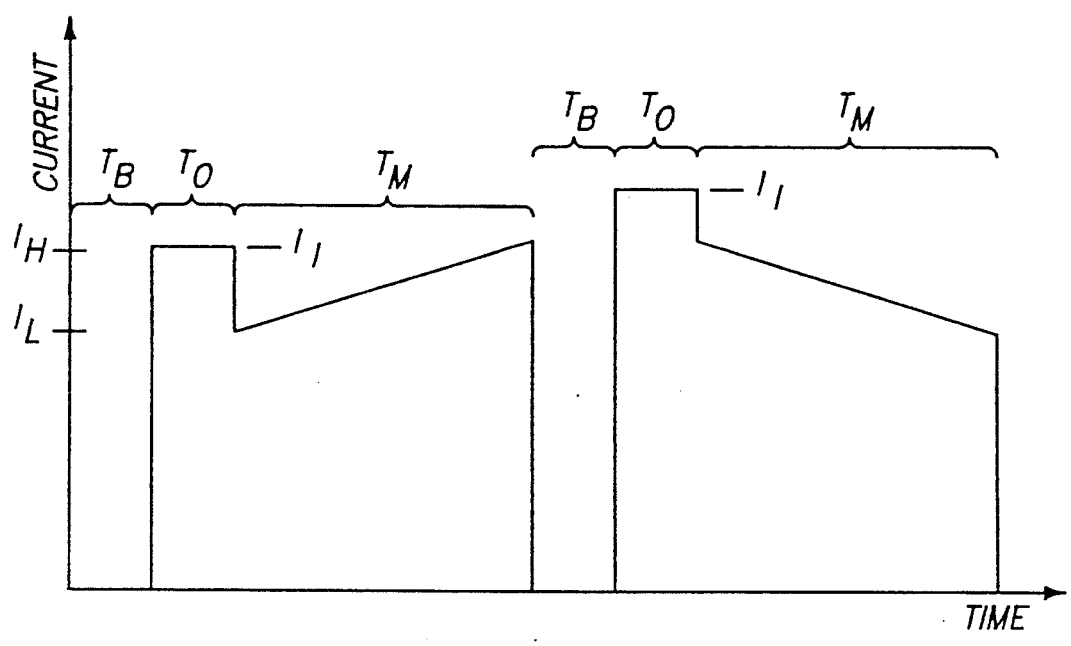
FIG. 3 is a diagram of laser drive current in accordance with a preferred embodiment of this invention.

More specifically, the laser drive current amplitude is repetitively modulated in a succession of modulation periods $T_M$ as shown in FIG. 3 to scan the laser beam wavenumber across an absorption line of the target gas. Drive current modulation period $T_M$ preferably includes linearly ramping the drive current amplitude from a beginning ramp current value to an ending ramp current value to cyclicly vary the laser emission across a wavelength or wavenumber modulation band. The modulation band at least partially spans the target gas absorption line.

The drive current modulation can take many forms, including that of a triangle waveform, as shown, or a sawtooth waveform. To form a triangle waveform successive drive current ramping steps alternate between low-to-high drive current ramping and high-to-low drive current ramping. During low-to-high drive current ramping the beginning ramp current is equal to $I_L$ and the ending ramp current is equal to $I_H$. $I_L$ is less than $I_H$. During high-to-low drive current ramping the beginning ramp current is equal to $I_H$ and the ending ramp current is equal to $I_L$.

To form a sawtooth waveform the beginning ramp current remains equal to one or either $I_L$ or $I_H$, with the ending ramp current remaining equal to the remaining one or $I_L$ or $I_H$. The beginning ramp current is thus consistently either less than or greater than the ending ramp current.

To determine measurement background intensity, the laser is disabled for a background-measuring period $T_B$ prior to each modulation period $T_M$. Laser disabling is accomplished by interrupting the laser drive current before each repetition of the drive current ramping. Laser 24 does not emit any light during the background-measuring period $T_B$. Accordingly, during this period measurement "zeros" or background intensities are measured at each of first and second radiation sensors 40 and 42. The subsequent laser transmission measurements are referenced to the background intensity measured during each cycle by subtracting the zero or background intensities from subsequent absolute radiation intensity measurements to obtain actual laser beam intensity measurements.

In prior art systems such disabling must be followed by a number of uninterrupted drive current modulations to restore the laser to an equilibrium excitation state. Any measurements performed during these modulations are inaccurate because of unpredictable laser emission wavenumbers and intensities as the laser warms up to the equilibrium operating temperature.

In the preferred embodiment of the invention described herein, however, accurate measurements are obtained during each and every modulation period, even while preceding each such period with a background-measuring period during which the laser is completely disabled. This is possible because of a unique and relatively brief overdriving period $T_O$ which takes place after each background-measuring period $T_B$ and immediately before each drive current modulation period $T_M$. The term "overdriving" refers to driving the laser with a current which is significantly greater than the beginning ramp current.

The amplitude $I_I$ of the increased drive current and the duration of the overdriving period are adjustable, being set to values which rapidly restore the laser to its pre-disabled excitation state and temperature prior to the drive ramping step. The overdriving period drastically shortens the time required to restore the laser to its equilibrium excitation state, thereby allowing accurate measurements to be taken during every drive current modulation step.

As an example, the drive current to laser 24 is typically modulated from about $I_L=220$ milliamperes to $I_H=223$ milliamperes. The modulation period is about $T_M=2$ milliseconds, and the overdriving period is about $T_O=100$ microseconds. During such an overdrive period, $I_I$ is equal to about 340 milliamperes. The background-measurement period is about $T_B=20$ microseconds.

Radiation intensity measurements are performed repetitively and continuously at first and second radiation sensors 40 and 42. Measurements are used for different purposes, depending on whether they are taken during the background intensity measurement period $T_B$, the current overdriving period $T_O$, or the modulation period $T_M$. The measurements are taken at discrete time intervals in relation to the current waveform supplied to laser 24. The successive measurements therefore correspond to specific laser emission wavelengths or wavenumbers.

Background intensity measurements, taken during background-measuring period $T_B$, are used as a reference for preceding or subsequent laser transmission intensity measurements. It is most preferable to use several such background measurements from each background-measurement period $T_B$ so that the measurements can be averaged or otherwise treated to eliminate random measurement noise.

Measurements made during the overdriving period $T_O$ are disregarded.

Measurements made during modulation period $T_M$ are used in calculating absorption properties of the sample and reference gases. During each modulation period $T_M$ a succession of intensity measurements $I_s$ and $I_r$ are made at sample and reference radiation sensors 40 and 42, respectively, at a series of discrete wavenumbers $v_i$, averaging the discrete intensity measurements at each discrete laser wavenumber $v_i$, over a predefined number of modulation periods $T_M$, to obtain average values for $I_s(v_i)$ and $I_r(v_i)$, corresponding to the sample and reference gases, respectively. Such averaging reduces the effects of random measurement noise.

Sensor control circuits 14 include circuits which coordinate the modulation period measurements with the digital-to-analog converters of laser control circuits 16, so that the measurements coincide in time with the discrete wavenumbers produced by laser 24 during its repetitive wavenumber modulation.

As a preferred example, 100 pairs of simultaneous discrete measurements are taken at a frequency of 50 kHz, during each period $T_B+T_O+T_M$, from first and second radiation sensors 40 and 42. Thus, the period of the triangle wave is four milliseconds. Discrete waveform data points are supplied to the digital-to-analog converters of laser control circuits 16 at the same 50 kHz frequency so that measurements and drive current waveform generation can be synchronized.

The object of the radiation intensity measurements is to obtain the absorbance functions $A_s(v_i)$ and $A_r(v_i)$ for the sample and reference gases, respectively, over a wavenumber modulation band from $v_0$ to $v_h$ which spans an absorption line from $v_1$ to $v_2$. Absorbance A is defined as the negative natural logarithm of transmittance T. Transmittance T, in turn, is defined as the fraction of laser light directed into the sample chambers which reaches sensors 40 and 42. Accordingly:

$$A(v_i) = -\ln T(v_i) = -\ln \frac{I(v_i)}{I_0(v_i)}$$

I is the actual, measured intensity at sensor 40 or 42. It can be referred to as the absorbed intensity since its value has been attenuated by gas absorption. $I_O$ represents the unabsorbed intensity—that which would be measured but for the presence of a gas absorption line.

Unabsorbed laser transmission intensity $I_O$ is assumed to be a linear function of $v$. To determine the function parameters, a straight line is fit over a plurality of absolute measurement values outside the target gas absorption line. More specifically, lower and upper unabsorbed laser transmission intensities are measured during the transmission wavenumber modulating step at lower and upper laser transmission wavenumbers which are below and above the target gas absorption line, or spanning $v_1$ and $v_2$. $I_O$ at intermediate wavenumbers between $v_1$ and $v_2$ is determined by interpolation. For best results, several intensity values, $I_O$, spanning the target gas absorption line are used to calculate the parameters of a "best-fit" straight line.

Figure 4:
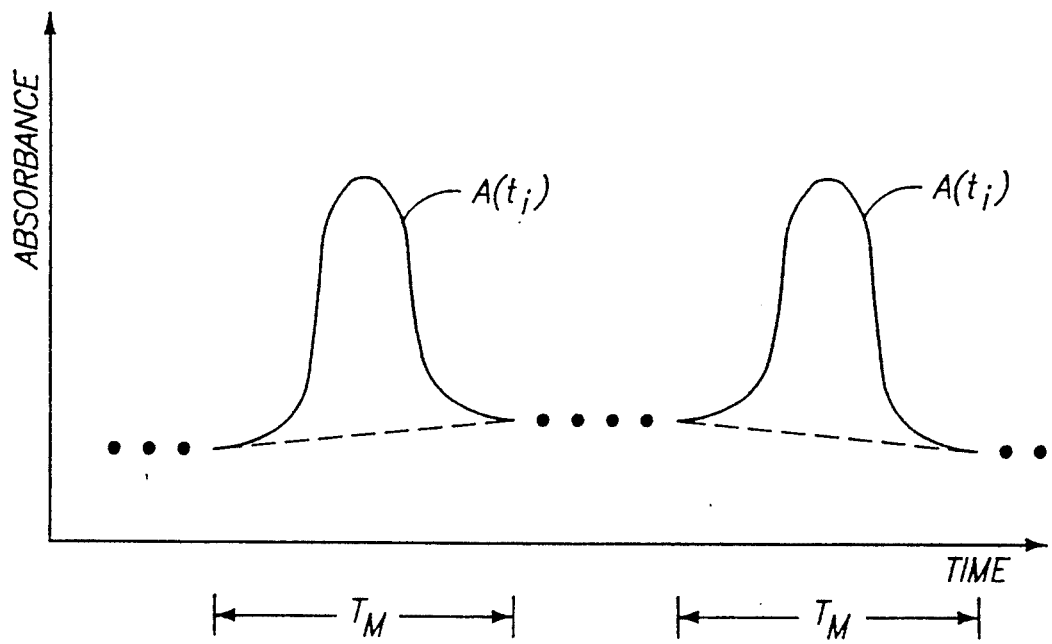
FIG. 4 is a diagram showing absorbance of the laser emission through either a sample gas or a reference gas in response to the laser drive current of FIG. 3.
Figure 5:
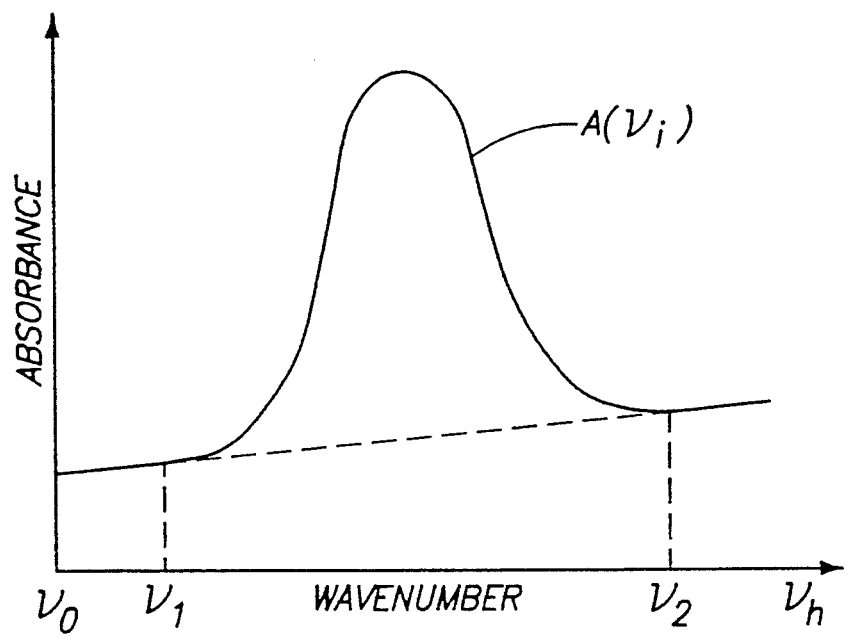
FIG. 5 is an enlarged diagram showing absorbance through a gas in response to one laser drive current modulation period of FIG. 3.

FIG. 4 illustrates a plot of the measured and calculated absorbance A as a function of time during two consecutive modulation periods $T_M$. FIG. 5 shows a plot of $A(v_i)$ during a single low-to-high wavenumber modulation period $v_O$ to $v_h$. The absorbance function reveals a target gas absorption line from wavenumber $v_1$ to $v_2$.

The relationship between molecular concentration of the gas and the absorbing effect of an absorption line is obtained by integrating the absorbance over the absorption line wavenumbers:

$$SNL = \int_{v_0}^{v_h} A(v_i) \delta v$$

In the above equation, S is the strength of the absorption line in cm/molecule, N is molecules/cm$^3$, and L is the absorbing path length of the laser beam in cm.

The above calculation is performed numerically by summing discrete values:

$$SNL = \Delta v \sum_{v_0}^{v_h} A(v_i)$$

To determine the concentration of target gas within the sample gas, the above absorbance functions for the sample gas and reference gas are ratioed:

$$\frac{SN_sL_s}{SN_rL_r} = \frac{\Delta v \sum A_s(v_i)}{\Delta v \sum A_r(v_i)}$$

This equation can be solved to find the molecular concentration of the sample gas, $N_s$, in terms of the known reference gas concentration $N_r$, the known physical dimensions of the analyzer $L_s$, and $L_r$, and the measured absorption functions $A(v_i)$:

$$N_s = \frac{N_r L_r \sum A_s(v_i)}{L_s \sum A_r(v_i)}$$

S is assumed to be equal for both the sample and reference gases. This assumption is valid as long as both gases are at equal temperatures and pressures, as they are in measurement assembly 20.

Additional accuracy is obtained through lowpass filtering of the logarithms of the sample and reference gas transmittances; more specifically, by convolution with a Gaussian impulse response as follows:

$$A(v_i) = - \sum_{-(v_h-v_0)/2}^{(v_h-v_0)/2} \ln(T(v_i - \beta)) e^{-(\beta^2/2\sigma^2)} \Delta\beta$$

Significant noise reduction and improved accuracy are obtained by ratioing the covariance of the sample gas filtered absorbance function and the reference gas filtered absorbance function with the variance of the reference gas filtered absorbance function. In analog form, the equation is as follows:

$$N_s = \frac{N_r L_r \int_{v_0}^{v_h} A_s(v) A_r(v) \delta v}{L_s \int_{v_0}^{v_h} A_r(v) A_r(v) \delta v}$$

After each wavenumber modulation or series of wavenumber modulations, the measured absorption of the target gas is analyzed to determine the center wavenumber of the absorption line. $v_O$ and $v_h$ are continuously adjusted, based on this determination, to center the wavenumber modulation about the target gas absorption line.

In compliance with the statute, the invention has been described in language more or less specific as to structural and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of operating a wavenumber-tunable laser to determine light absorption characteristics of a sample gas, wherein the laser emits a laser beam at a wavenumber which is variable in response to the amplitude of the drive current applied to it, the method comprising the following steps:

transmitting the laser beam through the sample gas to a first radiation sensor;

repetitively modulating the drive current amplitude from a beginning ramp current value to an ending ramp current value to cyclicly vary the laser beam wavenumber over a wavenumber modulation band while directing the laser beam through the sample gas, the modulation band at least partially spanning an absorption line of a target gas in the sample gas;

disabling the laser by interrupting the laser drive current before each repetition of the drive current modulating;

overdriving the laser with an increased drive current after the disabling step and before each repetition of the drive current modulating step to shorten the time required to restore the laser to its equilibrium excitation state; the increased drive current being greater than the beginning ramp current;

monitoring background intensity at the first radiation sensor during the disabling step; and monitoring the intensity of the laser beam at the first radiation sensor during the drive current modulating step.

2. The method of claim 1, wherein the step of monitoring the laser beam intensity during the drive current modulating step comprises the following additional steps:
   sensing absolute light intensity at the first radiation sensor; and
   subtracting background intensity from the absolute light intensity to obtain an actual laser beam intensity.

3. The method of claim 1, wherein successive drive current modulating steps alternate between low-to-high drive current modulation and high-to-low drive current modulation;
   the beginning ramp current being less than the ending ramp current during the low-to-high drive current modulation and the beginning ramp current being greater than the ending ramp current during the high-to-low drive current modulation.

4. The method of claim 1, wherein the beginning ramp current is less than the ending ramp current.

5. The method of claim 1, wherein the beginning ramp current is greater than the ending ramp current.

6. The method of claim 1, further comprising the following additional step:
   adjusting the increased drive current value to put the laser in an equilibrium excitation state before the drive current modulating step.

7. The method of claim 1, further comprising the following additional step:
   adjusting the duration of the overdriving step to put the laser in an equilibrium excitation state before the drive current modulating step.

8. The method of claim 1, further comprising the following additional step:
   repetitively adjusting the wavenumber modulation band so that the absorption line of the target gas is approximately centered within the modulation band.

9. The method of claim 1, further comprising the following additional steps:
   directing a portion of the laser beam through a reference gas to a second radiation sensor;
   monitoring the intensity of the laser beam at the second radiation sensor during the drive current modulating step; and
   monitoring background intensity at the second radiation sensor during the disabling step.

10. The method of claim 1, further comprising:
    directing the laser beam through a reference gas containing a known concentration of the target gas to a second radiation sensor;
    measuring the intensity of the laser beam at the second radiation sensor during the drive current modulating step at discrete laser wavenumbers which at least partially span the target gas absorption line;
    analyzing the measured intensity of the laser beam at the second radiation sensor to identify the target gas absorption line; and
    adjusting the wavenumber modulation band so that the target gas absorption line is approximately centered within the modulation band.

11. A method of determining laser transmittance through a sample containing an unknown quantity of a target gas, the laser transmittance being defined by absorbed laser transmissions through the sample and by corresponding unabsorbed laser transmissions, the method comprising:
    repetitively modulating the transmission wavenumber of a wavenumber-tunable laser about an absorption line of the target gas;
    disabling the laser by interrupting the laser drive current before each repetition of the transmission wavenumber modulating step;
    overdriving the laser after the disabling step and before each repetition of the transmission wavenumber modulating step;
    directing the laser transmissions through the sample;
    monitoring background intensity during the disabling step;
    measuring absorbed laser transmission intensities during the transmission wavenumber modulating step at discrete laser transmission wavenumbers corresponding to target gas absorption line wavenumbers;
    measuring lower and upper unabsorbed laser transmission intensities during the transmission wavenumber modulating step at lower and upper laser transmission wavenumbers which are below and above the target gas absorption line wavenumbers, respectively;
    determining the unabsorbed laser transmission intensities at wavenumbers between the lower and upper laser transmission wavenumbers from the lower and upper unabsorbed transmission intensities by interpolation.

12. The method of claim 11, further comprising the following additional step:
    referencing laser transmission measurements to the background intensity to obtain laser transmission intensities.

13. The method of claim 11, wherein the step of directing the laser transmissions through the sample includes directing the laser transmissions in a non-reflecting path through the sample.

14. The method of claim 11, wherein successive transmission wavenumber modulating steps alternate between a low-to-high wavenumber modulation and high-to-low wavenumber modulation.

15. The method of claim 11, wherein the transmission wavenumber modulating step is a low-to-high wavenumber modulation.

16. The method of claim 11, wherein the transmission wavenumber modulating step is a high-to-low wavenumber modulation.

17. The method of claim 11, wherein the overdriving step includes the step of:
    increasing the laser drive current amplitude after the disabling step and before each repetition of the transmission wavenumber modulating step, the increased drive current amplitude being greater than the laser drive current at the beginning of the wavenumber modulating step.

18. The method of claim 11, further comprising the following additional step:
    repetitively centering the transmission wavenumber modulation about the target gas absorption line.

19. The method of claim 11, further comprising the following additional step:
    averaging the measured absorbed and unabsorbed laser transmission intensities over a predefined number of transmission wavenumber modulation steps to obtain average absorbed and unabsorbed laser intensities.

20. A method of operating a wavenumber-tunable laser to determine concentration of a target gas within a sample, wherein the laser emits a laser beam at a variable wavenumber determined by the amplitude of the laser drive current, the method comprising the following steps:

repetitively modulating the laser drive current amplitude to vary the laser wavenumber about an absorption line of the target gas;

splitting the laser beam to direct a sample laser transmission through the sample and a reference laser transmission through a reference gas having a known concentration of the target gas;

disabling the laser by interrupting the laser drive current before each repetition of the drive current modulating step;

overdriving the laser with an increased drive current after the disabling step and before the drive current modulating step, the increased drive current being greater than the drive current at the beginning of the drive current modulating step;

monitoring background laser intensity during the disabling step; and simultaneously measuring the transmission intensities of the sample and reference beam transmissions during the drive current modulating step at discrete laser wavenumbers corresponding to target gas absorption line wavenumbers.

21. The method of claim 20, further comprising the following additional step:

subtracting background intensity from transmission intensity measurements during the transmission intensity measuring step.

22. The method of claim 20, wherein the laser beam splitting step includes directing the laser transmissions through non-reflecting paths through the sample and reference gas.

23. The method of claim 20, further comprising the following additional steps:

determining a reference gas absorbance from the reference beam transmission intensities;

determining a sample absorbance from the sample beam transmission intensities; and comparing the sample absorbance to the reference gas absorbance to determine the concentration of the target gas concentration in the sample.

24. The method of claim 20, further comprising the following additional steps:

analyzing the reference beam transmission intensities to identify the target gas absorption line; and adjusting the laser drive current modulation to center the laser wavenumber variations about the target gas absorption line.

25. The method of claim 20, further comprising the following additional step:

averaging the measured transmission intensities over a predefined number of drive current modulation steps to obtain average transmission intensities corresponding to the discrete laser wavenumbers.

26. The method of claim 20, further comprising the following additional step:

calculating sample and reference gas absorbances at wavenumbers corresponding to the target gas absorption line wavenumbers, said calculating being based on the transmission intensities measured during the drive current modulating step;

low-pass filtering the sample and reference gas absorbances; and ratioing the covariance of the sample and reference absorbances to the variance of the reference absorbance to determine the molecular concentration of the target gas in the sample without requiring temperature or pressure measurements of the gases.

27. The method of claim 20, further comprising the following additional steps:

calculating sample and reference laser absorbances at transmission wavenumbers corresponding to the target gas absorption line wavenumbers, said calculating being based on the transmission intensities measured during the drive current modulating step; and ratioing the sample and reference laser absorbances to determine the molecular concentration of the target gas in the sample without requiring temperature and pressure measurements of the gases.

28. The method of claim 27, wherein the step of calculating the absorbances includes the further step of integrating absorbed and unabsorbed laser transmission intensity measurements over a wavenumber modulation band at least partially spanning the target gas absorption line.

29. The method of claim 20, wherein the step of measuring the transmission intensities further includes the following steps:

measuring absorbed laser transmission intensities through the sample and reference gas at discrete laser wavenumbers which correspond to target gas absorption line wavenumbers; and measuring unabsorbed laser transmission intensities through the sample and reference gas at laser wavenumbers below and above the target gas absorption wavenumbers.

30. A tunable laser trace gas analyzer for determining the concentration of a target gas in a sample, comprising:

a wavenumber-tunable laser which emits a laser beam;

a first sample cell for receiving the sample, the first sample cell forming an optical path through the sample along a first longitudinal axis;

a reference cell for receiving a reference gas, the reference gas having a known concentration of the target gas, the reference cell forming an optical path through the reference gas along a second longitudinal axis, the reference cell being positioned relative to the first sample cell so that the first and second longitudinal axes intersect each other;

beam splitter means positioned at the intersection of the first and second longitudinal axes and in the path of the laser beam emitted by the laser for directing a first portion of the laser beam through the sample in the first sample cell along the first longitudinal axis and for directing a second portion of the laser beam through the reference gas in the reference cell along the second longitudinal axis;

a second sample cell positioned between the beam splitter means and the laser for receiving an additional volume of sample, the second sample cell being aligned along the first longitudinal axis to form an optical path also leading through the sample in the second sample cell; and first and second sensing means at remote ends of the first sample cell and the reference cell, respectively, for monitoring the intensities of the first and second portions of the laser beam after being transmitted through the first sample cell and the reference cell, respectively.

31. A gas analyzer as recited in claim 30, wherein the first and second sensing means are radiation sensors having active surfaces which are mounted an acute angle to the first and second longitudinal axes, respectively.

32. A gas analyzer as recited in claim 30, wherein the second sample cell is longitudinally aligned with the first sample cell, and wherein the beam splitter means comprises a beam splitting mirror positioned between the first sample cell and the second sample cell.

33. A tunable laser trace gas analyzer for determining the concentration of a target gas in a sample by comparison to a reference gas having a known concentration of the target gas, comprising:
   a wavenumber-tunable laser which emits a laser beam of varying wavenumber;
   a gas receiving assembly through which the laser beam is transmitted, the gas receiving assembly including first and second sample cells and a reference gas chamber;
   first and second radiation intensity sensors positioned at remote ends of the first sample cell and the reference gas chamber, respectively;
   a beam splitter within the gas receiving assembly adapted to direct a first laser beam portion to the first radiation intensity sensor and to direct a second laser beam portion to the second radiation intensity sensor; and
   the second sample cell being positioned between the beam splitter and the laser, the laser beam being directed through the second sample cell to the beam splitter.

34. A trace gas analyzer as recited in claim 33, wherein the beam splitter is positioned within the second sample cell to transmit the second laser beam portion through the reference gas chamber to the second radiation intensity sensor.

35. A trace gas analyzer as recited in claim 33, wherein the beam splitter is positioned within the second sample cell, the beam splitter directing the first portion of the laser beam through the first sample cell to the first radiation intensity sensor and directing the second laser beam portion through the reference gas chamber to the second radiation intensity sensor.

36. A trace gas analyzer as recited in claim 33, further comprising:
   laser control circuits which produce a timed sequence of discrete drive current magnitudes to vary the laser wavenumber; and
   sensor control circuits operably connected to the first and second radiation intensity sensors, the sensor control circuits being coordinated with the laser control circuits to take radiation intensity measurements in synchronism with the timed sequence of discrete drive current magnitudes.

37. A tunable laser trace gas analyzer for determining light absorption characteristics of a sample gas, comprising:
   a laser which emits a laser beam at a wavenumber which is variable in response to the amplitude of a drive current applied to the laser, the laser beam being transmitted through the sample gas;
   a first radiation sensor positioned relative to the laser to monitor the intensity of the laser beam after it is transmitted through the sample gas;
   laser control means for
   (a) supplying a drive current to the laser, the drive current having a variable amplitude;
   (b) repetitively modulating the drive current amplitude from a beginning ramp current value to an ending ramp current value to cyclicly vary the laser beam wavenumber over a wavenumber modulation band, the modulation band at least partially spanning an absorption line of a target gas in the sample gas;
   (c) disabling the laser by interrupting the laser drive current before each repetition of the drive current modulating; and
   (d) overdriving the laser with an increased drive current after the disabling step and before each repetition of the drive current modulating step to shorten the time required to restore the laser to its equilibrium excitation state, the increased drive current being greater than the beginning ramp current.

38. A trace gas analyzer as recited in claim 37 and further comprising means for:
   monitoring background intensity at the first radiation sensor while the laser control means is disabling the laser;
   monitoring absolute laser intensity at the first radiation sensor while the laser control means is modulating the drive current;

39. A trace gas analyzer as recited in claim 37 and further comprising means for:
   monitoring background intensity at the first radiation sensor while the laser control means is disabling the laser;
   monitoring absolute laser intensity at the first radiation sensor while the laser control means is modulating the drive current; and
   subtracting background intensity from the absolute light intensity to obtain an actual laser beam intensity.

40. A trace gas analyzer as recited in claim 37 wherein the laser control means alternates between a low-to-high drive current modulation and a high-to-low drive current modulation, wherein the beginning ramp current is less than the ending ramp current during the low-to-high drive current modulation and the beginning ramp current is greater than the ending ramp current during the high-to-low drive current modulation.

41. A trace gas analyzer as recited in claim 37 wherein the beginning ramp current is less than the ending ramp current.

42. A trace gas analyzer as recited in claim 37 wherein the beginning ramp current is greater than the ending ramp current.

43. A trace gas analyzer as recited in claim 37 wherein the laser control means is further for adjusting the increased drive current to put the laser in an equilibrium excitation state before modulating the drive current.

44. A trace gas analyzer as recited in claim 37 wherein the laser control means is further for adjusting the duration of overdriving to put the laser in an equilibrium excitation state before modulating the drive current.

45. A trace gas analyzer as recited in claim 37 wherein the laser control means is further for repetitively adjusting the wavenumber modulation band so that the absorption line of the target gas is approximately centered within the modulation band.

46. A trace gas analyzer as recited in claim 37 and further comprising:

beam splitter means for directing a first portion of the laser beam through the sample gas and for directing a second portion of the laser beam through a reference gas, the first radiation sensor being positioned to monitor the intensity of the first portion of the laser beam;

a second radiation sensor positioned relative to the laser to monitor the intensity of the second portion of the laser beam after it is transmitted through the reference gas.

47. A trace gas analyzer as recited in claim 37 wherein the laser control means is further for supplying a timed sequence of discrete drive current magnitudes to vary the laser wavenumber, the trace gas analyzer further comprising:

sensor control circuits operably connected to the first radiation sensor, the sensor control circuits being coordinated with the laser control means to take radiation intensity measurements in synchronism with the timed sequence of discrete drive current magnitudes.

48. A trace gas analyzer as recited in claim 37 wherein the laser control means is further for supplying a timed sequence of discrete drive current magnitudes to vary the laser wavenumber, the trace gas analyzer further comprising:

beam splitter means for directing a first portion of the laser beam through the sample gas and for directing a second portion of the laser beam through a reference gas, the first radiation sensor being positioned to monitor the intensity of the first portion of the laser beam;

a second radiation sensor positioned relative to the laser to monitor the intensity of the second portion of the laser beam after it is transmitted through the reference gas;

sensor control circuits operably connected to the first and second radiation sensors, the sensor control circuits being coordinated with the laser control means to take radiation intensity measurements in synchronism with the timed sequence of discrete drive current magnitudes.

* * * * *